United States Patent [19]

Graber-Gubert et al.

[11] Patent Number: 4,950,604
[45] Date of Patent: Aug. 21, 1990

[54] CULTURE OF A MICROORGANSIM OF THE GENUS KLEBSIELLA SP., HAVING A HIGH CONTENT OF RHAMNOSE

[75] Inventors: Marianne G. P. Graber-Gubert; Joseph C. A. Morin, both of Toulouse; Francis L. Duchiron, Avon; Pierre F. Monsan, Blagnac, all of France

[73] Assignee: Bioeurope, France

[21] Appl. No.: 281,542

[22] Filed: Dec. 8, 1988

[30] Foreign Application Priority Data

Dec. 11, 1987 [FR] France ................................. 87 17285

[51] Int. Cl.$^5$ ............................ C12R 1/22; C12N 1/20
[52] U.S. Cl. .................................. 435/252.1; 435/105; 435/852
[58] Field of Search ....................... 435/252.1, 852, 105

[56] References Cited

FOREIGN PATENT DOCUMENTS 0102535 3/1984 European Pat. Off. .

OTHER PUBLICATIONS

"Isolation of Microorganisms Producing 6-Deoxyhexose-Containing Polysaccharides", Marianne Graber-Gubert, et al., Systematic and Applied Microbiology, 10, 200–205 (1988).
Derwent Abs. 84–057319/10 Voelskow et al, EP-102535 (3-14-84).
Chem Abs CA09–51365 (7) Graber–Gubert et al., Syst. Appl. Microbiol., V10(2) p. 200–205, 1988.

Biotech Abs, 86–10266, Bryan et al, "Applied Environ Microbiol", 1986, 51, 6, 103–08.
"Variation in Composition and Yield of Exopolysaccharides Produced by Klebsiella sp. Strain K32 and Acinetobacter Calcoaceticus BD4", Barbara A. Bryan, et al., Applied and Environmental Microbiology, pp. 1304–1308, Jun. 1986.
Journal of Biotechnology, vol. 6, No. 4, Nov. 1987, pp. 293–306.
Applied and Environmental Microbiology, vol. 51, No. 6, Jun. 1986, pp. 1304–1308.
Collection Nationale de Cultures de Microorganisms (C.N.C.M.), Institut Pasteur, No. I-714 of Nov. 10, 1987.
French Search Report.

*Primary Examiner*—Herbert J. Lilling
*Attorney, Agent, or Firm*—Stevens, Davis, Miller & Mosher

[57] ABSTRACT

The invention relates to biotechnology.

It relates, in particular, to cultures of Klebsiella sp. microorganisms possessing the characteristics of the strain BEC 441 deposited under No. I-714 at the Collection Nationale de Cultures de Micro-organismes (National Collection of Microorganism Cultures) of the Institut Pasteur, as well as strains obtained from the strain BEC 441 by mutation, these strains being capable of producing polysaccharides rich in rhamnose by fermentation in a nutrient medium containing assimilable sources of carbon and of nitrogen and inorganic substances.

Application for the production of a mixture of monosaccharides having a high content of rhamnose.

1 Claim, 3 Drawing Sheets

FIG.1

| | CODE | 1 | 5 | 9 | |
|---|---|---|---|---|---|
| Control | | | | | 0 |
| Glycerol | | ▨ | ▨ | | 1 |
| Erythritol | | | | | 2 |
| D-Arabinose | | | | | 3 |
| L-Arabinose | | ▨ | ▨ | | 4 |
| Ribose | | | | | 5 |
| D-Xylose | | | | | 6 |
| L-Xylose | | | | | 7 |
| Adonitol | | | | | 8 |
| β Methyl-xyloside | | | | | 9 |
| Galactose | | ▨ | ▨ | | 10 |
| D-Glucose | | | ▨ | | 11 |
| D-Fructose | | | ▨ | | 12 |
| D-Mannose | | ▨ | ▨ | | 13 |
| L-Sorbose | | | | | 14 |
| Rhamnose | | ▨ | ▨ | | 15 |
| Dulcitol | | | | | 16 |
| Inositol | | ◩ | ▨ | | 17 |
| Mannitol | | | | | 18 |
| Sorbitol | | | | | 19 |
| α Methyl-D-mannoside | | | | | 20 |
| α Methyl-D-glucoside | | ▨ | ▨ | | 21 |
| N Acetyl glucosamine | | ◩ | ▨ | | 22 |
| Amygdaline | | | ▨ | | 23 |
| Arbutine | | | ▨ | | 24 |
| Esculine | | ▨ | ▨ | | 25 |
| Salicine | | | ▨ | | 26 |
| Cellobiase | | | ▨ | | 27 |
| Maltose | | | ▨ | | 28 |
| Lactose | | | ◩ | | 29 |
| Melibiose | | ▨ | ▨ | | 30 |
| Sucrose | | ▨ | ▨ | | 31 |
| Trehalose | | | | | 32 |
| Inuline | | | | | 33 |
| Melezilase | | | | | 34 |
| D-Raffinose | | ▨ | ▨ | | 35 |
| Amidon | | | | | 36 |
| Glycogene | | | | | 37 |
| Xylitol | | | ◩ | | 38 |
| β Gentiobiose | | ▨ | ◩ | | 39 |
| D-Turanose | | ◩ | | | 40 |
| D-Lyxose | | | | | 41 |
| D-Tagatose | | | | | 42 |
| D-Fucose | | | | | 43 |
| L-Fucose | | | | | 44 |
| D-Arabitol | | | | | 45 |
| L-Arabitol | | | | | 46 |
| Gluconate | | ▨ | | | 47 |
| 2 ceto-Gluconate | | ▨ | ◩ | | 48 |
| 2 ceto-Gluconate | | | ▨ | | 49 |

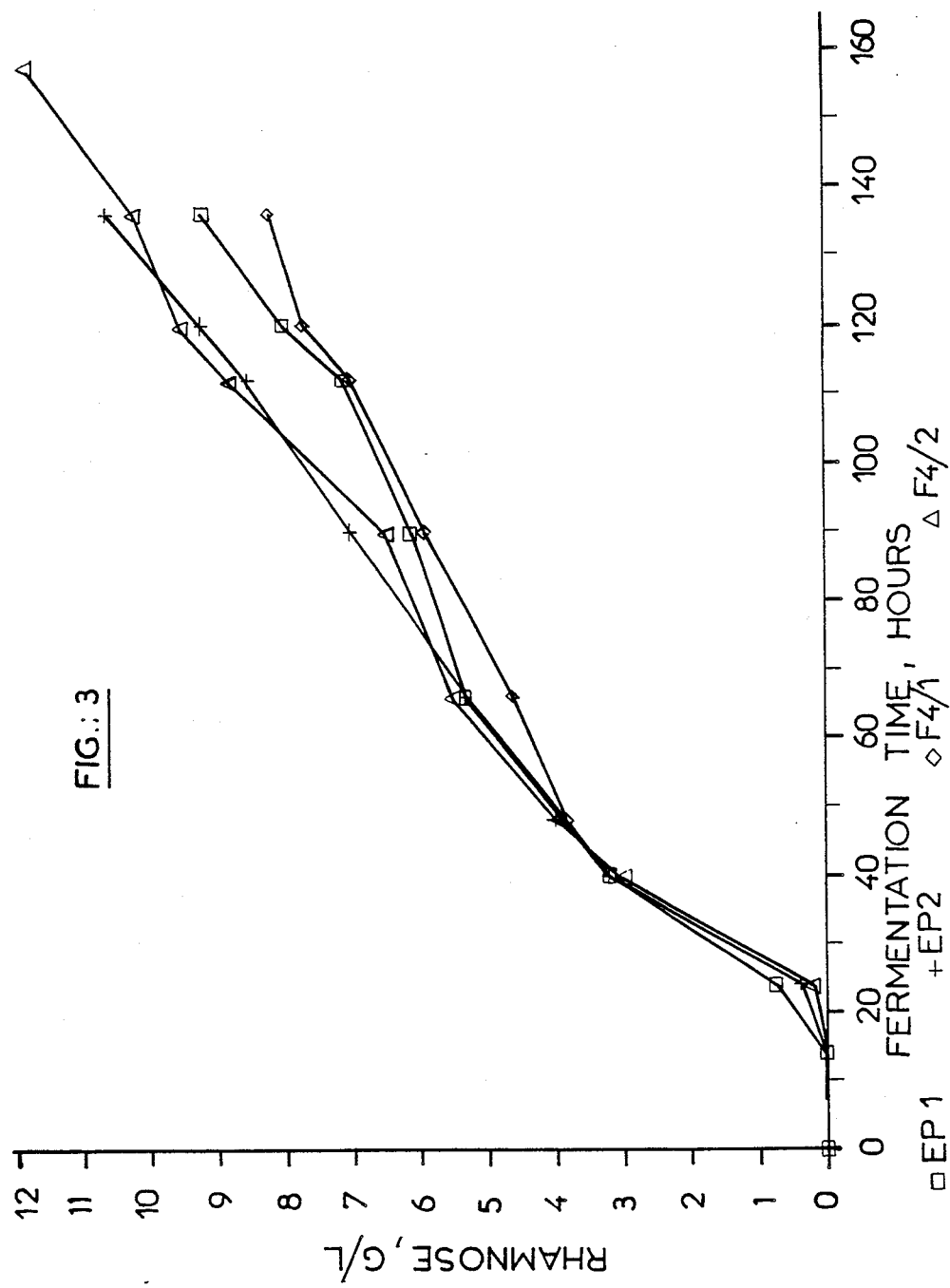
FIG.:3

CULTURE OF A MICROORGANSIM OF THE GENUS KLEBSIELLA SP., HAVING A HIGH CONTENT OF RHAMNOSE

The invention relates to a culture of a new microorganism of the genus Klebsiella sp. or of mutants of the latter, and to a process for producing a mixture of monosaccharides having a high content of rhamnose employing this culture.

It is known that some microorganisms of the genus Klebsiella can, under some growth conditions, produce polysaccharides, in particular exopolysaccharides, in a proportion of the order of a few tenths of a gramme per liter of growth medium, it being possible for rhamnose to constitute up to 66% of these exopolysaccharides. See in this connection the paper by B. A. Bryan, R. J. Linhardt and L. Daniels which appeared in the journal "Applied and Environmental Microbiology", vol. 51, No. 6, pages 1304–1308 (June 1986). However, the yield of rhamnose produced is too low to give rise to an industrial application.

The Applicant Company has now found that it was possible to produce rhamnose in much higher yields than those reported in the above paper by making use of a culture of a new microorganism of the genus Klebsiella sp.

The first subject of the present invention is hence to provide a culture of a new microorganism of the genus Klebsiella sp. which is capable of producing rhamnose in a high yield.

A second subject of the invention is to provide cultures of selected mutants of the said microorganism which are capable of producing rhamnose in a still better yield.

A third subject of the invention is to provide a process for producing a mixture of monosaccharides containing rhamnose.

More specifically, the invention relates to a culture of a new Klebsiella sp. microorganism possessing the characteristics of the strain BEC 441 deposited under number I-714, dated 10th Nov. 1987, at the Collection Nationale de Cultures de Micro-organismes (C.N.C.M) (National Collection of Microorganism Cultures) of the Institut Pasteur, 25, rue du Docteur Roux—75724 PARIS CEDEX 15, and capable of producing polysaccharides containing rhamnose, largely in the form of exopolysacchardies, by fermentation in a nutrient medium containing assimilable sources of carbon, of nitrogen and of inorganic substances.

BRIEF DESCRIPTION OF THE DRAWINGS

FIG. 1 is an enzyme profile demonstrating the ability of Klebsiella BEC 441 to metabolize various carbon sources;

FIG. 3 is a graph showing the rhamnose production versus the fermentation time for various mutant strains obtained from the strain BEC 441.

DETAILED DESCRIPTION OF THE INVENTION

Figure 2:
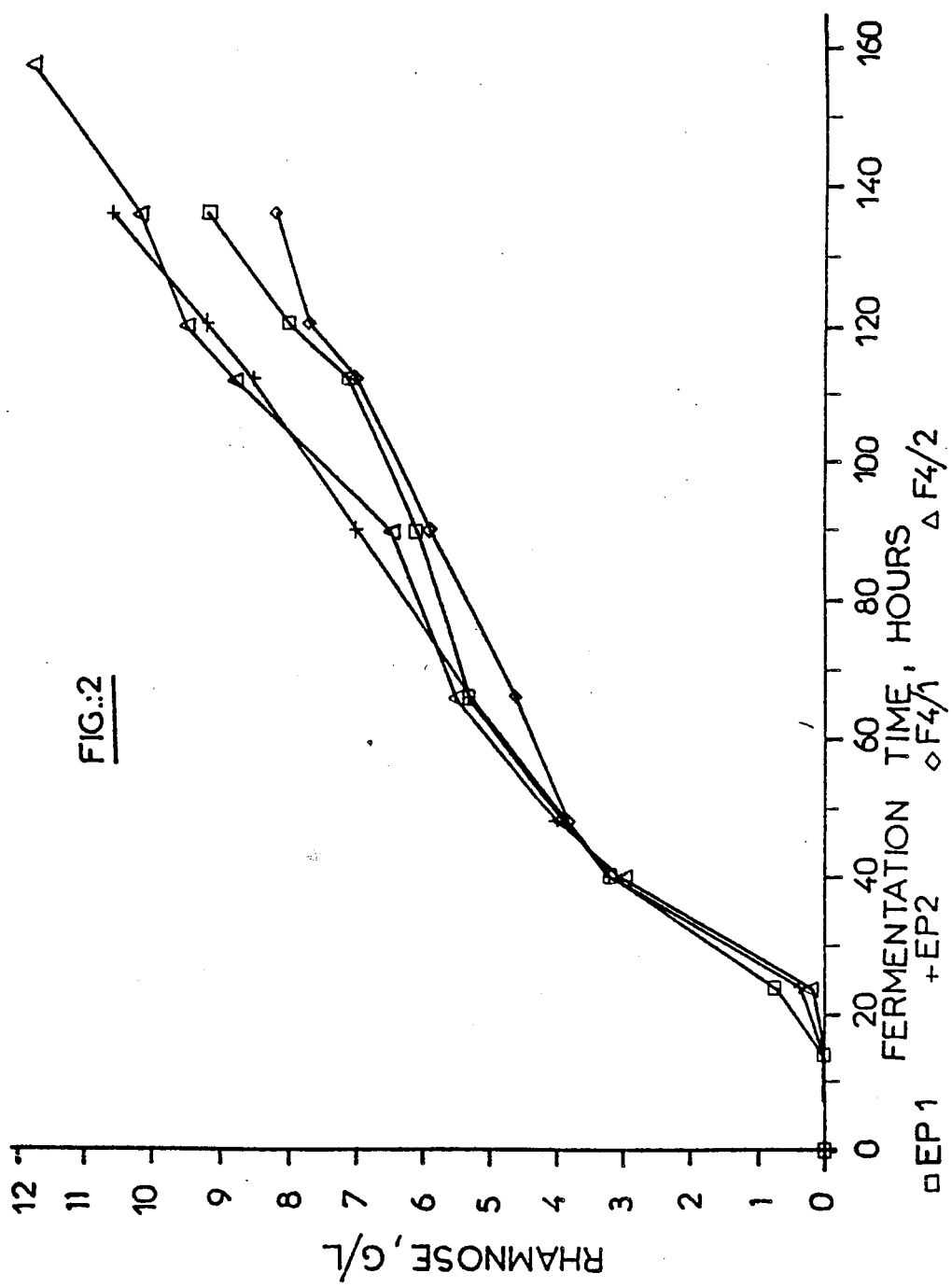
FIG. 2 shows comparative lipid profiles of Klebsiella BEC 441 and of Klebsiella terrigena CIP 80.07.

The new microorganism, which was isolated from sewage plant sludges, possesses the following characteristics:

BASIC ASPECTS

BACILLI HOMOGENEOUS IN FORM,
LARGE IN DIAMETER,
WITHOUT ANY SPECIAL ARRANGEMENT
MOBILITY —
GRAM STAINING
LYSIS WITH 3% KOH: +++
CULTURE VISIBLE IN DEEP AGAR: AERO/ANAEROBIC
CULTURE IN BROTH, 0% NaCl: +++
CULTURE IN BROTH, 2% NaCl: +++
CULTURE IN BROTH, 4% NaCl: +++
CULTURE IN BROTH, 6% NaCl: ++
CULTURE IN BROTH, 8% NaCl: +
CULTURE IN BROTH, 10% NaCl: —
[BASE MEDIUM: PYG (peptone: 10 g/l; yeast extract: 3 g/l; glucose: 1 g/l)]
CULTURE at 10° C.: +++
CULTURE at 20° C.: +++
CULTURE at 41° C.: +++
CULTURE at 45° C.: —
[BASE MEDIUM: BHI (brain, heart infusion, Diagnostic Pasteur)]
RAPID AND LUXURIANT CULTURE ON ORDINARY AGARS:
WHITISH, THICK, SMOOTH, SPREAD COLONIES
of 8–10 MM IN DIAMETER (COLUMBIA AGAR,
30° C., AIR, 4 DAYS, INCUBATION)
PROTOTROPHIC CULTURE
ACID PRODUCTION FROM GLUCOSE: +++
GAS PRODUCTION FROM GLUCOSE:
at 10° C.: +++ d
at 30° C.: +++
at 41° C.: —
VOGES - PROSKAUER REACTION: +++
NITRATE REDUCTASE: +++
NITRITE REDUCTASE: +
THIOSULPHATE REDUCTASE: —
TETRATHIONATE REDUCTASE: —
UREASE: +++
INDOLE PRODUCTION: —
PHENYLALANINE DEAMINASE: —
TRYPTOPHAN DEAMINASE: —
"ARGININE DIHYDROLASE": —
"ORNITHINE DECARBOXYLASE": —
"LYSINE DECARBOXYLASE": —
γ-GLUTAMYLTRANSFERASE: +++
HYDROLYSIS OF oNPb-GALACTOSIDE: +++
HYDROLYSIS OF pNPb-XYLOSIDE: —
HYDROLYSIS OF pNPb-GLUCURONATE: —
HYDROLYSIS OF INSOLUBLE STARCH: +
HYDROLYSIS OF TWEEN 80: —
LIPASE ON EGG YOLK AGAR: —
EXTRACELLULAR DNASE: —
GELATINASE (FRAZIER): —
CASEINASE: —
ACIDIFICATION IN API ® 50 CH (sold by API System S.A., La Balme-les-Grottes, 38390 Montalieu-Vercieu, France)
SUSPENSION MEDIUM: MTL (M63 medium below + peptone 5 g/l + yeast extract 0.5 g/l)
INDICATOR: PHENOL RED
READINGS: DAYS, 1, 5, 9
 The results are summarized in FIG. 1.
 CULTURES IN M63 MEDIUM (inorganic medium for the study of carbon sources, whose composition is:

| | |
|---|---|
| $KH_2PO_4$: | 3.9 g/l |
| $K_2HPO_4$: | 11.2 g/l |
| $(NH_4)_2SO_4$: | 2 g/l |
| $MgSO_4.7H_2O$: | 0.2 g/l |
| $FeSO_4.7H_2O$: | 0.05 g/l |

IN THE PRESENCE OF
D-GLUCOSE: +++
ACETIC Ac.: +++
MALONIC Ac.: —
CITRIC Ac.: +++
3-HYDROXYBENZOIC Ac.: —
L-HYDROXYPROLINE: —
REACTIONS AT 30° C. AIR
EXPLANATIONS OF THE SYMBOLS:
—: REACTION OR CULTURE NEGATIVE
w: WEAK
d: DELAYED

-continued

BASIC ASPECTS

+: POSITIVE
++: VERY POSITIVE
+++: SPECIALLY INTENSE

CHEMOTAXONOMIC ASPECTS

COMPOSITION IN RESPECT OF POLAR LIPIDS
Comparative analysis by thin layer chromatography on silica
Extraction process: chloroform/methanol 1:2
one-dimensional chromatography:
migration solvent: chloroform/methanol/water/acetic ac.
65:25:4:0.8

| | |
|---|---|
| visualization of phospholipids: | ammonium molybdate |
| aminated lipids: | ninhydrin |
| glycolipids: | α-naphthol |
| total lipids: | vanillin/$H_2SO_4$ | reference strain:
mfl 290: *KLEBSIELLA TERRIGENA* CIP 80.07
The chromatograms obtained are reproduced in FIG. 2.

The Klebsiella sp. I. 714 strain gives a positive reaction in the Neufeld reaction (capsule swelling) when tested against the K 14 and K 44 anti capsular sera. It gives a negative reaction against several other anti capsular sera such as K1 to K13, K 15, K 17 to K 43, K 46, K 47, K 50, K51, K 54, K 55, K 59 to K 62, K 64 to K 67, and K 70 to K 72. The I. 714 strain gives a weakly positive Neufeld reaction against the K 16, K 45, 48, K 49, K 52, K 53, K 56 to K 58, K 68 and K 69 sera. The I. 714 strain is thus related to the K 14 and K 44 serotypes.

The present invention also relates to the cultures of mutants of the microorganism Klebsiella sp. BEC 441. Useful mutants may be obtained by the simple selection of spontaneous mutants isolated from a previous culture in the fermenter, or alternatively by subjecting a culture of Klebsiella sp. BEC 441 to the action of high-energy radiation (UV rays, X-rays, for example) or of a chemical agent [for example ozone, nitrous acid, NTG (N-methyl-N,-nitro-N-nitrosoguanidine) or EMS (ethyl methane sulphonate)] for the purpose of killing a large portion of the microorganisms, by culturing the surviving microorganisms and by selecting those that produce more polysaccharide.

The present invention relates, in addition, to a process for obtaining a mixture of monosaccharides having a high content of rhamnose, which consists in fermenting a culture of Klebsiella sp. BEC 441, or of selected mutants of the latter, in a nutrient medium comprising a carbon source, a nitrogen source and suitable mineral salts, at a pH of approximately 6 to 8, at a temperature of approximately 30° to 35° C., with aeration and stirring, for 2 to 12 days, in isolating the resulting polysaccharides from the fermentation medium and then in hydrolysing these polysaccharides and in adjusting the pH of the resulting hydrolysate in the range from 5 to 9 approximately.

The invention also relates to the rhamnose produced using a culture according to the invention.

As a carbon source, substances such as sorbitol, mannitol, glucose, glycerol and mixtures thereof may be used, no limitation being implied At the present time, sorbitol is preferred. It is not essential to use a chemically pure source of carbon. It is possible, for example, to use technical grade sorbitol containing, inter alia, mannitol as impurities.

As a guide, from 5 to 100 g of carbon source per liter of nutrient medium, and preferably 10 to 50 g/l, may be used.

As a nitrogen source, substances such as casein peptone (obtained by acid or enzymatic hydrolysis of casein), maize steep liquor, yeast extract, soybean peptone, potato flour, L-phenylalanine, threonine, ammonium sulphate and mixtures thereof may be used, no limitation being implied. At the present time, casein peptone, maize steep liquor and potato flour are preferred. L-Phenylalanine also gives good results, but has the drawback of being relatively expensive.

As a guide, from 0.5 to 10 g of nitrogen source per liter of nutrient medium, and preferably 1 to 5 g/l, may be used.

An important parameter is the carbon/nitrogen ratio by weight in the nutrient medium. It is advantageous to use a ratio of at least 5 and which can range up to 100 and more.

An inorganic salts, it is necessary to include a magnesium salt, for example $MgSO_4$, and at least one phosphate salt, for example chosen from $M_2HPO_4$ where M is an alkali metal or an ammonium ion. The magnesium salt may be present, for example, in the proportion of 0.1 to 0.3 g/l while the phosphate salt may be present, for example, in the proportion of 2 to 15 g/l. It is advantageous to use a mixture of $M_2HPO_4$ and $MH_2PO_4$, since such a mixture enables the pH of the nutrient medium to be adjusted and, in addition, acts as a buffer.

The temperature of the fermentation medium can range from 30° to 35° C., and is preferably 32°-33° C. The pH of the medium must be between 6 and 8, and is preferably in the region of neutrality (pH 7).

The aeration conditions must be sufficient to maintain the partial pressure of oxygen above the fermentation medium. In general, an aeration of the order of 0.3 to 3 VVM (volume of air/volume of medium/minute) will be sufficient.

It is also necessary to keep the fermentation medium well stirred, in order to avoid an excessive thickening of the latter. In general, stirring at a speed of 300 to 1500 rpm will be suitable.

It is, moreover, advantageous, although not essential, to incorporate in the nutrient medium a surfactant agent which is non-toxic for the microorganism, in order to facilitate the separation of the polysaccharides from the fermentation medium. An example of a useful surfactant agent is the nonionic surfactant agent sold commercially under the registered trade mark "Tween 80" (polyoxyethylene-sorbitol monooleate). For example from 0.5 to 2 g/l and preferably approximately 1 g/l of this agent may be incorporated.

It is also advantageous to incorporate in the nutrient medium a small amount of yeast extract (if it is not used as a main nitrogen source) in order to provide a supply of vitamins.

The fermentation time will generally be of the order of 2 to 12 days, according to the working conditions and the objective of polysaccharide concentration to be attained.

The isolation of the polysaccharides produced, which are in the form of exopolysaccharides and polysaccharides bound to the cells, may be carried out, for example, by subjecting the fermentation medium to a heat treatment at 70°-120° C. approximately for 10 minutes to 1 hour approximately (to extract the fraction of the polysaccharides bound to the cells), and then by centrifuging in the cold state and collecting the clear supernatant layer. This layer contains virtually the whole of the polysaccharides. It is then possible, if desired, to precipitate the polysaccharides in the collected supernatant layer by adding a non-solvent organic liquid such as acetone or a lower alcohol such as ethanol or propanol, thereafter separate the precipitate by filtration or centrifugation and finally dry it. As a variant, the supernatant layer may be lyophilized.

The polysaccharides produced by Klebsiella sp. BEC 441 (I. 714) are comprised of a hexasaccharide repeating unit. This hexasaccharide comprises rhamnose, galactose and glucuronic acid in molar ratios of 3:2:1, respectively. It comprises a side chain branched at the position 3 on the galactose. At the branching site of the said side chain is directly attached the uronic acid which is part of the side chain. This latter ends by a rhamnose residue.

A hydrolysis of the polysaccharides by means of a strong acid such as $H_2SO_4$ or HCl is then performed in order to convert the polysaccharides to monosaccharides, and the pH of the hydrolysate is thereafter adjusted with a base such a NaOH or KOH in order to obtain a pH in the range from 5 to 9 approximately, and preferably close to neutrality.

The hydrolysis may be performed directly on the clear supernatant layer, or on the dried or lyophilized product. The hydrolysis may be performed, for example, using $H_2SO_4$ at 100° C. for 6 hours, the final acid concentration in the volume treated being approximately 2 N.

Typically, the neutralized hydrolysate has the following monosaccharide composition:

| | |
|---|---|
| rhamnose | 64–80 (percentage in molar ratio) |
| glucose | 2–22 (percentage in molar ratio) |
| galactose | 12–21 (percentage in molar ratio) |
| glucuronic acid | 0–12 (percentage by weight) |

If so desired, the rhamnose may be isolated from the other monosaccharides by known techniques for separating monosaccharides. As a guide, the neutralized hydrolysates may be subjected to a separation by chromatography on an ion exchange column after being desalted and replaced in a buffer suited to the ion exchange resin used. An example of a suitable resin is Dowex 1×4 with the use of a borate buffer, but many other resins are usable.

The mixture of monosaccharides having a high content of rhamnose or the rhamnose isolated from this mixture is a useful starting material for the synthesis of taste modifiers or flavourings such as furaneol and its derivatives.

Moreover, the polysaccharides produced by the culture of the invention have the uses of polysaccharides in general, and may be used, for example, as a stabilizer, suspending, dispersant or thickening agent, film-forming agent, water-retention agent, coagulant, colloid, lubricant, for example in washing powders, textiles, adhesives, paper, paints and foods, as well as for enhanced oil recovery.

In order to illustrate the present invention, the following non-limiting examples are given below.

In each of these examples, an inoculum of the culture of the invention having an optical density of 0.15 at 600 nm was employed in a proportion of 10 milliliters/liter of fermentation medium.

EXAMPLE 1

A fermentation medium having the following composition was placed in a laboratory fermenter (fermenter model 105500 sold by the company BIOLAFITTE, Saint-Germain en Laye, France, having a capacity of 2 liters):

| | |
|---|---|
| sorbitol | 20 g/l |
| phenylalanine | 1 g/l |
| $MgSO_4.7H_2O$ | 0.2 g/l |
| $K_2HPO_4$ | 9 g/l |
| $KH_2PO_4$ | 3 g/l |
| Tween ® 80 | 1 g/l |
| extract of baker's yeast | 20 mg/l |

The inoculum specified above was added to this medium, and a fermentation was performed under the following conditions

| | |
|---|---|
| Temperature | 30° C. |
| Aeration | 0.5 VVM |
| Stirring | 400 to 600 rpm |
| Initial pH | 7 (not controled). |

After 7 days' fermentation, the rhamnose content was 3 g/l of fermentation medium, as determined by spectrophotometry. 50 g/l of sorbitol and 5 g/l of phenylalanine were then added to the medium. Four days later, the rhamnose content was 5.5 g/l.

EXAMPLE 2

A fermentation was performed in the same equipment as in Example 1, but using the following fermentation medium:

| | |
|---|---|
| sorbitol | 20 g/l |
| phenylalanine | 2 g/l |
| Tween ® 80 | 1 g/l |
| $MgSO_4.7H_2O$ | 0.2 g/l |
| $K_2HPO_4$ | 9 g/l |
| $KH_2PO_4$ | 3 g/l |
| Yeast extract | 20 mg/l |

The fermentation conditions were the same as in Example 1.

After 8 days' fermentation, a rhamnose content of 5.5 g/liter of fermentation medium was obtained.

EXAMPLE 3

Example 2 was repeated, except that the proportions of sorbitol and of phenylalanine were raised to 50 g/l and 5 g/l respectively.

After only 7 days' fermentation, a rhamnose content of 5.5 g/liter of the fermentation medium could thus be obtained.

EXAMPLE 4

This example describes the preparation of mutant strains that are hyperproductive of polysaccharides rich in rhamnose from the starting strain BEC 441, by a treatment with UV rays.

A culture of the strain BEC 441 is produced on the following medium:

| | |
|---|---|
| sorbitol | 10 g/l |
| phenylalanine | 1 g/l |
| Tween ® 80 | 1 g/l |
| $MgSO_4.7H_2O$ | 0.2 g/l |
| $K_2HPO_4$ | 9 g/l |
| $KH_2PO_4$ | 3 g/l |

After 4 days' incubation at 30° C. with aeration (0.5 VVM), 5 ml of this culture are centrifuged (5 min at rpm), and the pellet is taken up in 5 ml of physiological solution.

The cell suspension thereby obtained is introduced into a Petri dish and placed under a UV lamp (Philips 5 W) at a distance of 20 cm. Throughout the exposure period, manual agitation is performed. After 1 min of exposure, the surviving cells (approximately 1% of the total cells) are reintroduced into 20 ml of the medium described above and incubated for 3 hours at 30° C. in order to produce a phenotypic expression.

After this incubation, the cells are plated in a dish on the following medium:

|   |   |
|---|---|
| sorbitol | 50 g/l |
| phenylalanine | 5 g/l |
| Tween ® 80 | 1 g/l |
| $MgSO_4.7H_2O$ | 0.2 g/l |
| $K_2HPO_4$ | 9 g/l |
| $KH_2PO_4$ | 3 g/l |
| agar | 15 g/l |

After one week's incubation at 30° C., the mutant colonies which have produced more polysaccharides are identified by the presence of a mucoid area around the colony which is larger than on the non-mutant colonies.

These colonies are isolated, then multiplied in the same way as the initial strain, and stored.

EXAMPLE 5

This example describes the preparation of mutant strains that are hyperproductive of polysaccharides rich in rhamnose from the starting strain BEC 441, by a treatment with ozone.

A 1-liter culture is produced in a fermenter on the liquid medium and under the conditions described in Example 4.

After 4 days' incubation, a treatment with ozone is performed using a laboratory ozonizer. For this purpose, the air entering the fermenter is diverted via the ozonizer before being introduced into the fermenter. After 1 hour's treatment, the aeration is reestablished.

The number of viable cells is determined before and after the treatment, the level of survivors after the treatment being approximately 10%.

A phenotypic expression is carried out by leaving the cells to incubate for a further 3 hours after the treatment. The cells are then plated on a Petri dish to test for hyperproductive mutants; this test is carried out in the same manner as in Example 4.

EXAMPLE 6

This example illustrates the production of polysaccharides rich in rhamnose using mutant strains.

Identification of the strains used:

EP 1 and EP 2:

are obtained from the strain BEC 441 by UV mutagenesis, as described in Example 4.

$F_4$ 1 and $F_4$ 2:

are spontaneous mutants isolated from a previous culture in the fermenter. The spontaneous mutant colonies hyperproductive of polysaccharides rich in rhamnose are identifiable by the presence of a mucoid area surrounding the colony which is larger than on the non-mutant colonies.

| Culture medium employed: | |
|---|---|
| sorbitol | 50 g/l |
| casein peptone | 4.5 g/l |
| phenylalanine | 0.1 g/l |
| yeast extract | 0.05 g/l |
| Tween ® 80 | 1 g/l |
| $MgSO_4.7H_2O$ | 0.2 g/l |
| $K_2HPO_4$ | 1.8 g/l |
| $KH_2PO_4$ | 0.6 g/l |
| Culture conditions in the fermenter: | |
| Temperature | 32° C. |
| pH | maintained to 7.0 with 1 N NaOH |
| Aeration | 0.5 VVM |
| Stirring | 400 to 1000 rpm |

The production of rhamnose is followed day by day, and curves are plotted for rhamnose production in terms of the fermentation time for each of the mutant strains used. The curves obtained are shown in FIG. 3.

It is seen that it is possible to obtain up to 12 g of rhamnose per liter of fermentation medium after less than 7 days of fermentation.

We claim:

1. Cultures of biologically pure Klebsiella sp. microorganism possessing the characteristics of the strain BEC 441 deposited under No. I-714 at the Collection Nationale de Cultures de Microorganismes (National Collection of Microorganism Cultures) of the Institut Pasteur, as well as strains obtained from the strain BEC 441 by mutation, said strains being capable of producing polysaccharides comprised of hexasaccharide repeating units consisting essentially of rhamnose, galactose and glucuronic acid units in molar ratio of 3:2:1, respectively, by fermentation in a nutrient medium containing assimilable sources of carbon and of nitrogen, and inorganic substances.

* * * * *